(12) United States Patent
Heras et al.

(10) Patent No.: US 10,209,166 B2
(45) Date of Patent: Feb. 19, 2019

(54) SYSTEM AND METHOD FOR PROCESSING BIOLOGICAL SPECIMENS

(71) Applicants: Alfonso Heras, Santa Barbara, CA (US); Jose Vargas, Santa Barbara, CA (US); Jack Novak, Goleta, CA (US)

(72) Inventors: Alfonso Heras, Santa Barbara, CA (US); Jose Vargas, Santa Barbara, CA (US); Jack Novak, Goleta, CA (US)

(*) Notice: Subject to any disclaimer, the term of this patent is extended or adjusted under 35 U.S.C. 154(b) by 426 days.

(21) Appl. No.: 14/945,264

(22) Filed: Nov. 18, 2015

(65) Prior Publication Data

US 2016/0139010 A1    May 19, 2016

Related U.S. Application Data

(60) Provisional application No. 62/081,315, filed on Nov. 18, 2014.

(51) Int. Cl.
| | |
|---|---|
| *G01N 1/00* | (2006.01) |
| *G01N 1/31* | (2006.01) |
| *G02B 21/34* | (2006.01) |
| *B01L 9/00* | (2006.01) |
| *G01N 35/00* | (2006.01) |

(52) U.S. Cl.
CPC .............. *G01N 1/312* (2013.01); *B01L 9/52* (2013.01); *G01N 35/00029* (2013.01); *G02B 21/34* (2013.01); *B01L 2300/0822* (2013.01); *B01L 2400/0406* (2013.01); *G01N 2035/00138* (2013.01); *G01N 2035/00237* (2013.01); *G01N 2035/00356* (2013.01)

(58) Field of Classification Search
CPC ........................................................ B01L 9/52
See application file for complete search history.

(56) References Cited

U.S. PATENT DOCUMENTS

| | | |
|---|---|---|
| 4,199,613 A | 4/1980 | Johnson |
| 4,731,335 A | 3/1988 | Brigati |
| 4,777,020 A | 10/1988 | Brigati |
| 4,798,706 A | 1/1989 | Brigati |
| 4,801,431 A | 1/1989 | Cuomo et al. |
| 4,975,250 A | 12/1990 | Mordecki |
| 5,002,736 A | 3/1991 | Babbitt et al. |
| 5,023,187 A | 6/1991 | Koebler et al. |
| 5,279,791 A | 1/1994 | Aldrich et al. |
| 5,554,536 A | 9/1996 | Rising |
| 5,569,607 A | 10/1996 | Simon et al. |
| 6,188,474 B1 | 2/2001 | Dussault et al. |

(Continued)

FOREIGN PATENT DOCUMENTS

WO    WO2010074915    7/2010

*Primary Examiner* — Jyoti Nagpaul
(74) *Attorney, Agent, or Firm* — Cislo & Thomas, LLP

(57) ABSTRACT

A system for processing biological specimens mounted on microscope slides by adding and removing processing fluids from microscope slides by means of capillary action using a slide holder capable of holding multiple microscope slides, and a spacer positioned in between two slides of a slide pair to create a capillary gap. A capillary gap adjuster can be used to pinch and release one end of the slide pair to create a pulsatile action to mix the reagent within the capillary gap. The system may further include a reagent holder, an absorbent pad, a series of reagent baths, and an incubator for holding one or more slide holders.

20 Claims, 16 Drawing Sheets

(56) References Cited

U.S. PATENT DOCUMENTS

| | | |
|---|---|---|
| 7,138,270 B2 | 11/2006 | Papkovsky et al. |
| 7,303,725 B2 | 12/2007 | Reinhardt et al. |
| 7,470,541 B2 | 12/2008 | Copeland et al. |
| 7,481,980 B2 | 1/2009 | Gausepohl |
| 7,550,298 B2 | 6/2009 | Towne et al. |
| 7,615,371 B2 | 11/2009 | Kram |
| 7,718,435 B1 | 5/2010 | Bogen et al. |
| 7,754,147 B2 | 7/2010 | Ljungmann et al. |
| 7,820,381 B2 | 10/2010 | Lemme et al. |
| 7,901,634 B2 | 3/2011 | Testa et al. |
| 7,952,798 B2 | 5/2011 | Ljungmann et al. |
| 7,998,408 B2 | 8/2011 | Ljungmann et al. |
| 8,007,721 B2 | 8/2011 | Angros |
| 8,048,373 B2 | 11/2011 | Reinhardt et al. |
| 8,178,350 B2 | 5/2012 | Erickson et al. |
| 8,585,989 B2 | 11/2013 | Rich et al. |
| 8,877,485 B2 | 11/2014 | Larsen et al. |
| 8,911,815 B2 | 12/2014 | Kram et al. |
| 2008/0194034 A1 | 8/2008 | Erickson et al. |
| 2013/0203100 A1 | 8/2013 | Otter et al. |
| 2014/0169931 A1* | 6/2014 | Diepersloot ............... B01L 9/52 414/800 |
| 2014/0273088 A1* | 9/2014 | Winther ................. G01N 1/312 435/40.52 |
| 2015/0071833 A1 | 3/2015 | Kram et al. |
| 2015/0293341 A1 | 10/2015 | Kram et al. |

\* cited by examiner

SYSTEM AND METHOD FOR PROCESSING BIOLOGICAL SPECIMENS

CROSS-REFERENCE TO RELATED APPLICATION

This patent application claims the benefit of U.S. Provisional Patent Application Ser. No. 62/081,315, entitled "Capillary Gap Device for Processing Microscope Slides," filed Nov. 18, 2014, which application is incorporated in its entirety here by this reference.

TECHNICAL FIELD

The present invention relates generally to systems for processing biological specimens mounted on microscope slides by adding and removing processing fluids from microscope slides by means of capillary action.

BACKGROUND

Immunohistochemistry ("IHC") is a method for testing cells or tissue samples for the presence of specific molecules. These methods are useful in both research and diagnostic applications for analyzing cell or tissue specimens. For example, in a diagnostic setting the molecular profile of a tissue can provide evidence of a particular disease state, such as cancer. These IHC methods first comprise the step of preparing an antibody to the particular molecule of interest. An antibody is a protein that is made to specifically recognize and combine with a molecule of interest. The molecule of interest is referred to as an antigen, and an antibody can specifically recognize and bind to its antigen. The specificity of this reaction allows an investigator to infer the presence of the antigen (target molecule, or target) whenever the antigen-antibody reaction takes place. For example, in the diagnosis of cancer, a specific antibody to a cancer-associated antigen is placed in contact with cells or tissue sample suspected of being cancer, If the antigen-antibody reaction occurs, this indicates that the suspected tissue was in fact cancer, The steps of IHC typically include fixing a tissue by placing a tissue into a fixative such as formalin. The fixative has two primary effects, First, it rapidly stops all metabolic activity in the cells so there is no degradation of molecular structures or changes in morphology, and secondly it makes the tissue rigid so that it can be embedded in hot paraffin and still retain its overall structure. Fixation with formalin is accomplished by inducing chemical cross-linking within and between molecules, particularly protein molecules. Other suitable fixation methods may also be used, Next, the fixed tissue is embedded in hot paraffin which is allowed to cool to form a solid paraffin block containing the embedded tissue. The paraffin block is then cut into thin slices of the tissue. A thin tissue section is applied onto a microscope slide such that the tissue can be subsequently examined under the microscope once the staining reaction has been completed.

The microscope slide may be treated with the attached tissue with a processing fluid that contains a paraffin solvent, such that the paraffin that is used to embed and mount the tissue onto the microscope slide is removed. Then the microscope slide is typically treated with a series of alcohols to remove the paraffin solvent, finally the microscope slide is treated with a series of aqueous solutions to rehydrate the tissue back into its native state. These steps, called deparaffinization, effectively remove the paraffin while leaving the tissue rehydrated and still adherent to the microscope slide.

The next step typically involves applying an antigen retrieval ("AR") solution to expose antigens within the tissue. In the process of fixing the tissue, the molecular structure of the protein is frequently altered such that an antibody reagent will no longer react with its target r molecule. In order to overcome this limitation, AR methods were developed that have the ability to reverse the cross-links and restore the molecules to a more native configuration that can be recognized by the antibody reagent. This step of the process is called heat-induced AR, or simply AR.

The tissue is then typically treated on a microscope slide with a chemical to block endogenous enzyme activity. A specific (primary) antibody may be applied onto a tissue sample. The primary antibody is allowed enough time to bind to its antigen (if present). The bound primary antigen may be visualized by adding an enzyme linked to a secondary reagent. A substrate/chromogen is added which reacts with the enzyme to form a colored (dye) end-product. The colored end-product is visualized by viewing the tissue sample under the microscope. If the colored end-product is observed, then the tissue contained the suspected antigen. If no colored end-product is observed, then the tissue did not contain the suspected antigen.

Another method commonly used for studying cells or tissues is called In Situ Hybridization ("ISH"). In this method the target that is being analyzed is a nucleic acid (either DNA or RNA). The probe that is used to detect the nucleic acid is a complementary strand of nucleic acid. The rationale behind this approach is that complementary strands of nucleic acids will bind to each other. Therefore, it is possible to synthetically construct a probe with a complementary nucleic acid sequence to the target nucleic acid. The target nucleic acid may be a gene or gene fragment, it may be nucleic acid of a bacterial or viral pathogen, or it may be a gene product, such as an mRNA. The binding of a probe to a target nucleic acid is indicative of the presence of the target nucleic acid in the cells or tissues under investigation. For example, the amplification of a gene called Her2/neu is a primary driver for the development of certain breast cancers. By applying a probe to Her2/neu gene in a breast cancer specimen, it can be determined whether that breast cancer had an abnormal amplification (>2) of the Her2/neu gene or whether that breast cancer had a normal copy number (=2) of the Her2/neu gene. This information can then be used to direct the most optimal therapy.

The steps of ISH typically include fixing a tissue by placing a tissue into a fixative such as formalin. The fixed tissue is then embedded in hot paraffin which is allowed to cool to form a solid paraffin block containing the embedded tissue. Thin slices of the tissue are cut from the paraffin block. A thin tissue section is then applied onto a microscope slide such that the tissue can be subsequently examined under the microscope once the staining reaction has been completed.

The microscope slide is treated with the attached tissue to a processing fluid that contains a paraffin solvent, such that the paraffin that is used to embed and mount the tissue onto the microscope slide is removed. The microscope slide is treated with a series of alcohols to remove the paraffin solvent, and the microscope slide is treated with a series of aqueous solutions to rehydrate the tissue back into its native state. These steps call deparaffinization, effectively remove the paraffin while leaving the tissue rehydrated and still adherent to the microscope slide.

The next step involves applying a target retrieval ("TR") solution to expose nucleic acids within the tissue. In the process of fixing the tissue, the molecular structure of the nucleic acids is frequently altered such that a probe reagent will no longer react with its target molecule. In order to overcome this limitation TR methods were developed that have the ability to reverse the cross-links and restore the molecules to a more native configuration that can be recognized by the probe reagent. This step of the process is called heat-induced TR. In another related procedure the tissue may be treated with an enzyme that accomplishes essentially the same thing as the heat-induced TR. If this process is utilized it is referred to as enzyme pretreatment or enzyme TR.

A tissue on a microscope slide may then be treated with a chemical to block endogenous enzyme activity. A specific probe may be applied onto a tissue sample that has a nucleic acid sequence complementary to the target being detected. The probe is allowed enough time to bind to its target (if present). The bound probe is visualized by adding an enzyme linked to a secondary reagent. A substrate/chromogen is added which reacts with the enzyme to form a colored (dye) end-product. The colored end-product is visualized by viewing the tissue sample under the microscope.

The use of the capillary gap method for processing slides is riot new to the field of immunohistochemistry. In the late 1980's David Brigati (U.S. Pat. No. 4,731,335) described the adaptation of an automated instrument that was designed to remove paraffin from tissue samples and to rehydrate the tissue samples. This device held a number of microscope slides vertically in a slide holder which were then submerged into a series of reagent baths to first dissolve the paraffin and then to rehydrate the slides in preparation for immunohistochemistry. In Brigati's adaptation, a custom microscope slide with raised spacers was needed where the slides were in mounted in the vertical slide holder in pairs facing each other, so that a capillary gap was formed between the two adjacent facing slides. Instead of submerging the slides into a bath, the bath system was adapted to form shallow troughs that contained only a few hundred microliters of reagents. When the ends of the slide pairs contacted the reagent troughs, the liquid was drawn up between the slide pairs by capillary action. Likewise, in order to remove reagents the ends of the slide pairs were brought into contact with an absorbent material which caused a reverse capillary flow and withdrew the reagents from the capillary space. Major drawbacks of the Brigati method were 1) there was a requirement for a specialized slide that contained raised areas to form the capillary space (the available commercial microscope slides were not suitable for the Brigati method), and 2) the resultant staining was not uniform. Typically the bottom portion of the specimen stained darker than did the top part of the specimen. The uneven staining was the result of lack of mixing of the processing fluids within the capillary space.

For the foregoing reasons there is a need for a new system for processing biological specimens that can utilize standard, economical microscope slides, while producing consistent results.

SUMMARY

The invention generally relates to a system for processing biological specimens, which includes a slide holder capable of holding multiple microscope slides as slide pairs, gap spacer in between the slides of each slide pair to define a capillary gap. In some embodiments, the slide holder is provided as a kit with a reagent holder, an absorbent pad, a series of reagent baths, and/or an incubator for holding one or more slide holders and heating reagents.

An object is to provide a system for processing biological specimens mounted on microscope slides, for example, staining biological specimens mounted on microscope slides by adding and removing processing fluids from microscope slides by means of capillary action.

Another object is to provide a system that can stain biological specimens on microscope slides by the method of immunohistochemistry.

Another object is to provide a system that can stain biological specimens on microscope slides by the method of in situ hybridization.

Another object is to provide a system that contains a microscope slide holder that provides an adjustable space between adjacent microscope slides thereby creating a capillary gap between the adjacent slides.

Another object is to provide a system that can add and remove processing fluids from biological specimens on microscope slides by use of capillary action.

Another object is to provide a system that contains a microscope slide holder that allows adjustment of the capillary gap between adjacent slides such that the size of the gap controls the amount of fluid drawn into the capillary gap.

Another object is to provide a system that contains microscope slide holder that facilitates filling of fluids into the capillary gap between adjacent microscope slides by reducing the size of the capillary gap and facilitating drainage of fluid from the capillary gap by increasing the size of the gap.

Another object is to provide a system that contains a microscope slide holder that facilitates drainage of fluid from the capillary gap by increasing the size of the gap, which decreases the rinsing required between reactive steps.

Another object is to provide a system that contains a microscope slide holder that facilitates the upward and downward flow of fluid within the capillary gap of adjacent microscope slides by a process of increasing and decreasing the gap space, thereby facilitating a pulsatile motion of the fluid contained therein.

Another object is to provide a system that accomplishes all of the above objects by utilizing ordinary microscope slides for both bottom and cover slides to create the capillary gap.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

DETAILED DESCRIPTION OF THE INVENTION

Figure 1A:
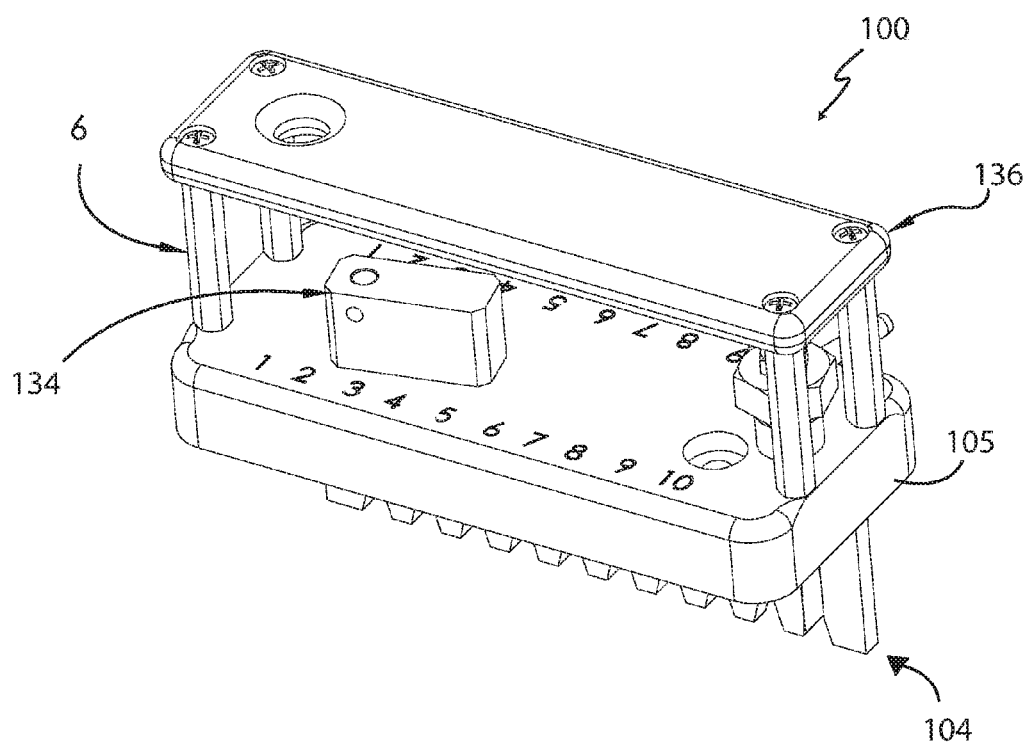
FIG. 1A shows a top perspective view an embodiment of a slide holder of the present invention.
Figure 1B:
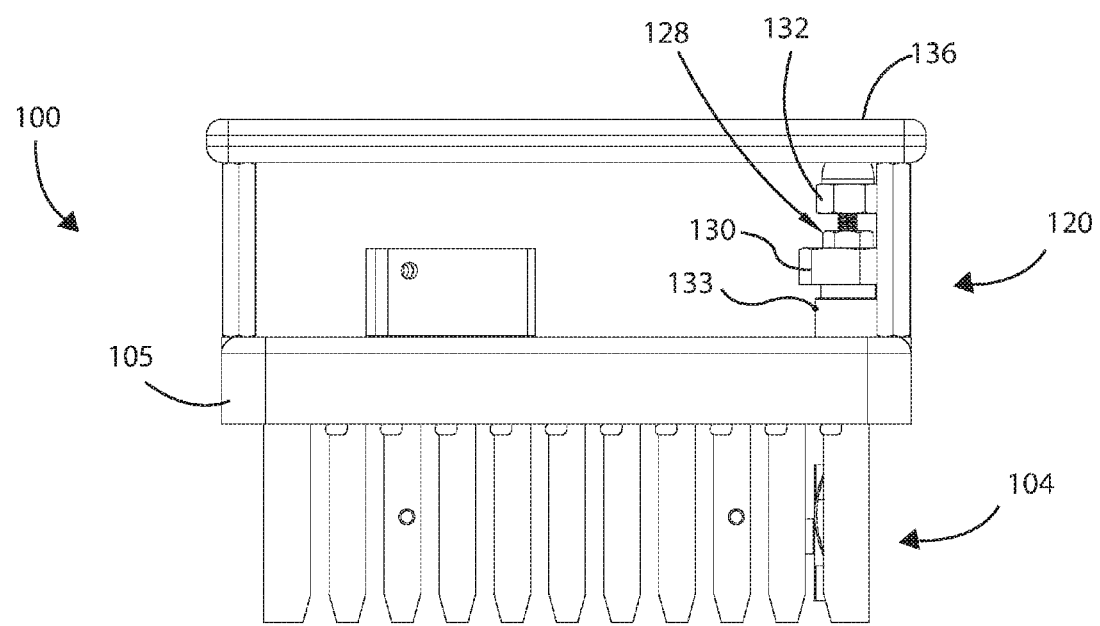
FIG. 1B shows a side elevation view of the slide holder shown in FIG. 1A.
Figure 1C:
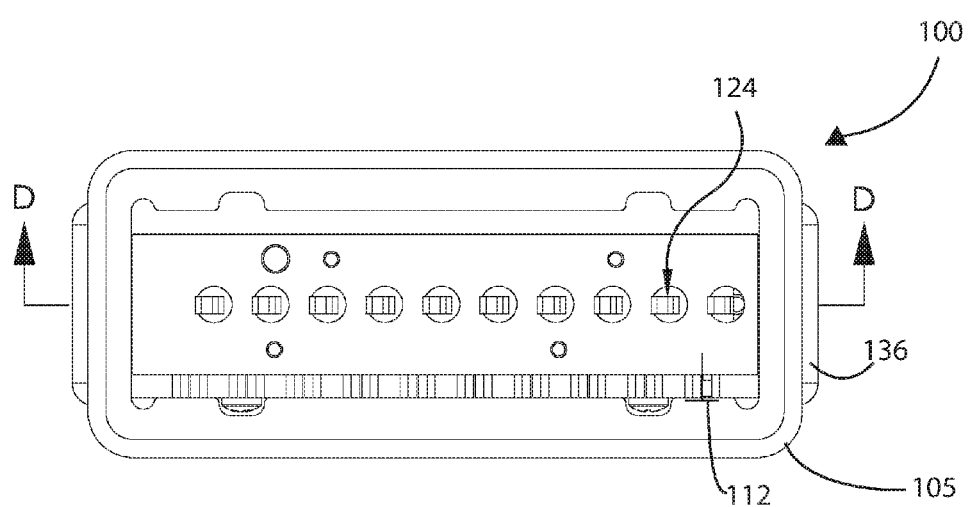
FIG. 1C shows a bottom view of the slide holder shown in FIG. 1A.
Figure 1D:
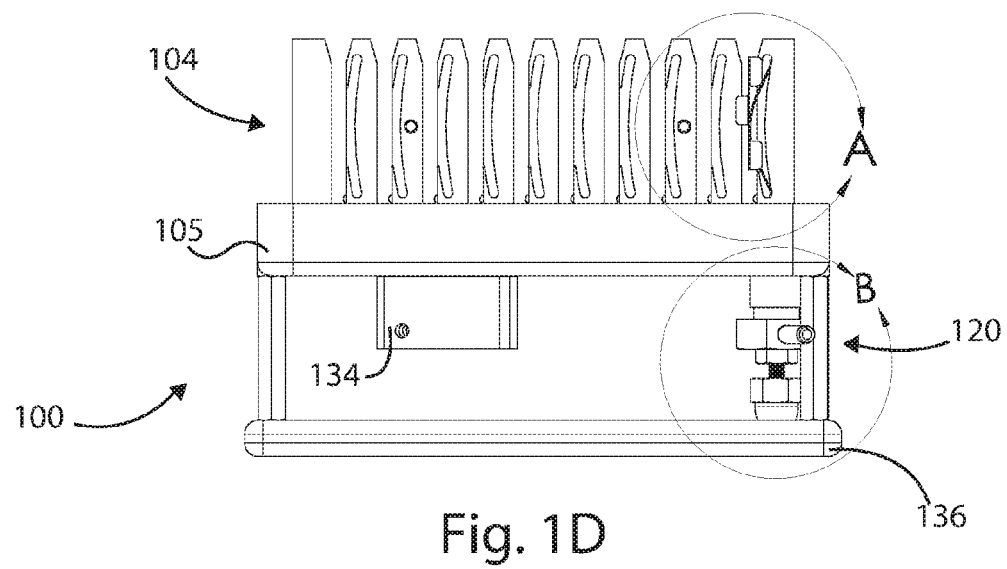
FIG. 1D shows another side elevation view of the slide holder shown in FIG. 1A.
Figure 1E:
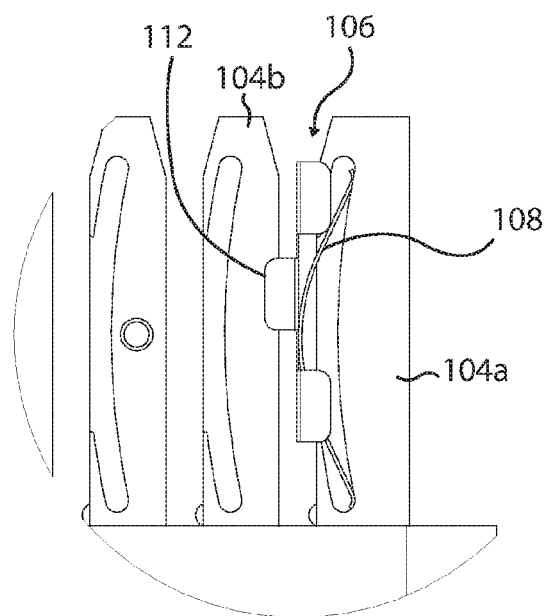
FIG. 1E shows a close-up view of section A shown in FIG. 1D.

The detailed description set forth below in connection with the appended drawings is intended as a description of presently-preferred embodiments of the invention and is not intended to represent the only forms in which the present invention may be constructed or zed. The description sets forth the functions and the sequence of steps for constructing and operating the invention in connection with the illustrated embodiments. It is to be understood, however, that the sane or equivalent functions and sequences may be accomplished by different embodiments that are also intended to be encompassed within the spirit and scope of the invention.

In this respect, before explaining at least one embodiment of the invention it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Turning now descriptively to the drawings, in which similar reference characters denote similar elements throughout the several views, the figures illustrate a slide holder capable of holding multiple microscope slides as slide pairs with a capillary gap defined between two slides within a slide pair, a reagent holder, an absorbent pad, a series of reagent baths, and an incubator for holding one or more slide holders.

Slide Holder

Figure 4:
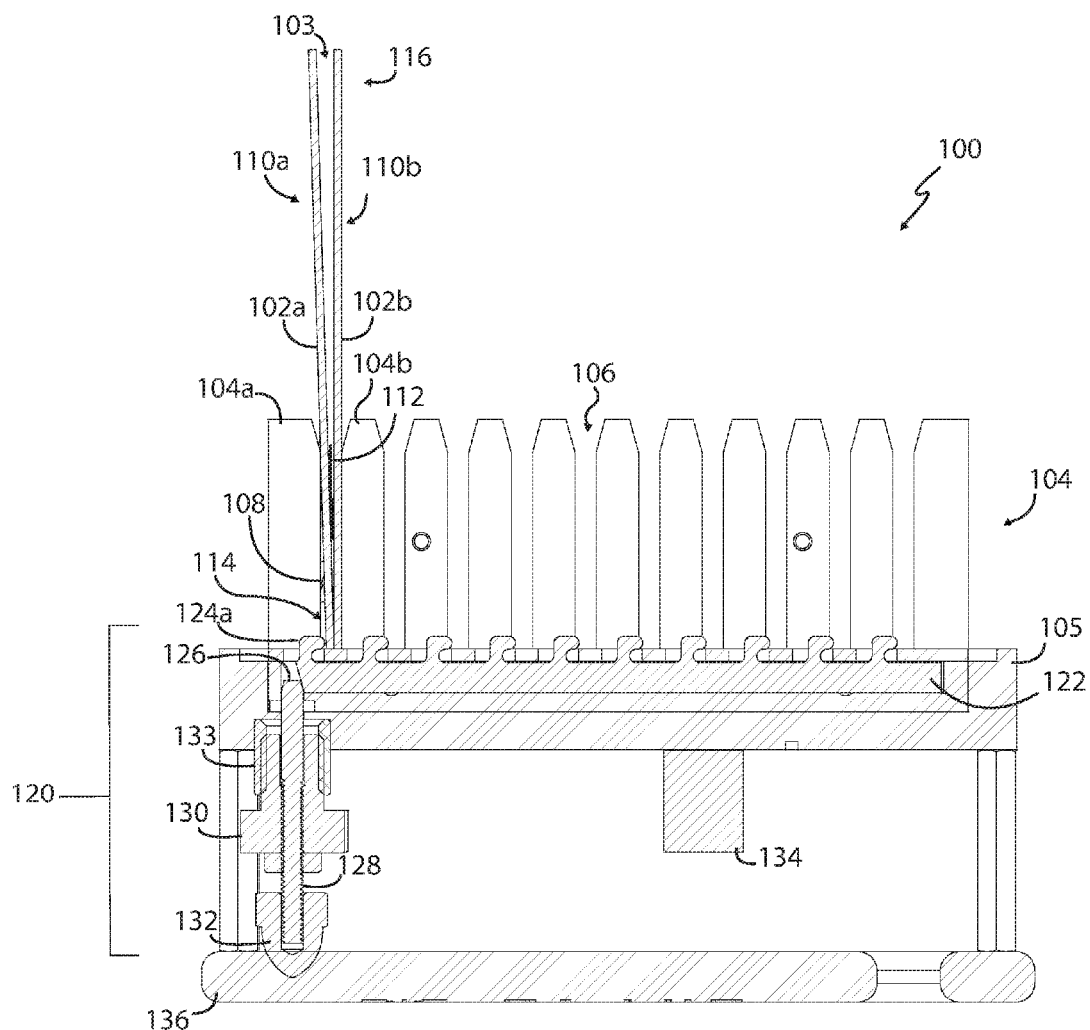
FIG. 4A shows a bottom view of another embodiment of the slide holder.
FIG. 4B shows a cross-section taken through line D-D in FIG. 1C.

With reference to FIGS. 1A-4, the slide holder 100 is configured for holding multiple microscope slides 102, in particular, standard, unmodified microscope slides, arranged in slide pairs 102a, 102b such that a capillary gap 103 is formed between the slides of the slide pairs 102a, 102b. To hold the microscope slides 102, the slide holder 100 comprises a plurality of posts 104 serially arranged on a cover 105, wherein a groove 106 is defined in between adjacent posts 104a, 104b for receiving one slide pair 102a, 102b. Retaining springs 108 may be used to secure each slide pair 102a, 102b to their respective post pairs 104a, 104b. For each slide pair 102a, 102b, at least one retaining spring 108 biases against a first post 104a and a first outer surface 110a of the slide pair 102a, 102b as shown in FIGS. 3B and 4. In some embodiments, a second retaining spring 108 may bias against a second post 104b and a second outer surface 110b of the slide pair 102a, 102b so that the inner surfaces 118a, 118b are pressed towards each other. Therefore, the slide pair may be sandwiched between two retaining springs 108 biased against a post 104a, 104b. Note, the designation of a slides outer surface 110a, 110b or the inner surface 118a, 118b is not limiting, but rather descriptive as to how two slides are arranged together. Therefore, either side of a slide 102 can be considered the inner surface or the outer surface depending on which of these surfaces of the slides are adjacent to each other.

To create the capillary gap 103, a spacer 112 is placed in between each slide of a slide pair 102a, 102b (i.e against the inner surfaces 118a, 118b). Unlike prior art devices that require specialized microscope slides or other specialized surfaces that oppose the slide holding the tissue sample, due to the spacer 112, the present invention can utilize standard rectangular microscope slides for both opposing slides. The spacer 112 may be positioned closer to one end (referred to as the first end 114) of the slide pair 102a, 102b than the opposite end (referred to as the second end 116). The first end 114 is the end that is inserted in between a pair of posts 104a, 104h. The second end 116 of the slide pair 102a, 102h opposite the first end 114 remains free. The specimen to be analyzed may be placed closer to the second end 116 of the slide pair 102a, 102b than the first end. But depending on the configuration of the spacer, the specimen to be analyzed may be placed at any location on the slide not covered by the spacer and not subject to contact by the cover slide.

Figure 1F:
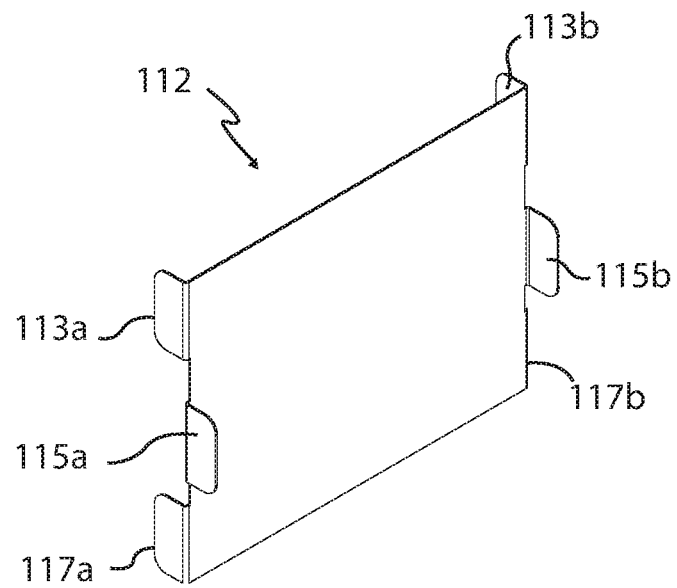
FIG. 1F shows a perspective view of an embodiment of a spacer.

The spacer 112 can be any material k enough to create a capillary gap in between the two slides of a slide pair 102a, 102b. Preferably, the spacer 112 spans across the entire width of the slide pair 102a, 102b. With reference to FIG. 1F, in some embodiments, the spacer 112 is a shire defined by a flat plate having a pair of forward tabs 113a, 113b projecting perpendicularly from the surface of the flat plate in the same direction but on opposite sides of the flat plate. The forward tabs 113a, 113b are spaced apart about the width of a microscope slide 102 so that one of the slides 102a can fit in between the forward tabs 113a, 113b width-wise.

Similarly, the shim may have a pair of rearward tabs 115a, 115b. Like the forward tabs 113a, 113b, the rearward tabs 115a, 115b project perpendicularly from the surface of the flat plate in the same direction as each other at opposite ends of the flat plate, but in a direction opposite the forward tabs 113a, 113b. The rearward tabs 115a, 115b are spaced apart about the width of a microscope slide 102 so that the other slide 102b can fit in between the rearward tabs 115a, 115b width-wise. The forward tabs 113a, 113b and the rearward tabs 115a, 115b minimize any side to side movement of the slides 102 while in the slide holder 100. Any number of additional tabs 117a, 117b can project in either the forward direction or the rearward direction for additional support.

Figure 1G:
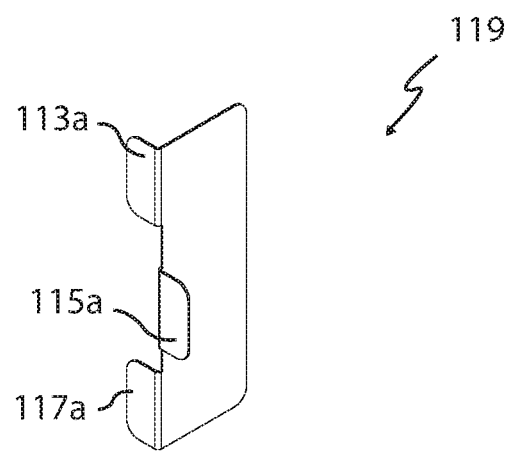
FIG. 1G shows a perspective view of another embodiment of a spacer.
Figure 1H:
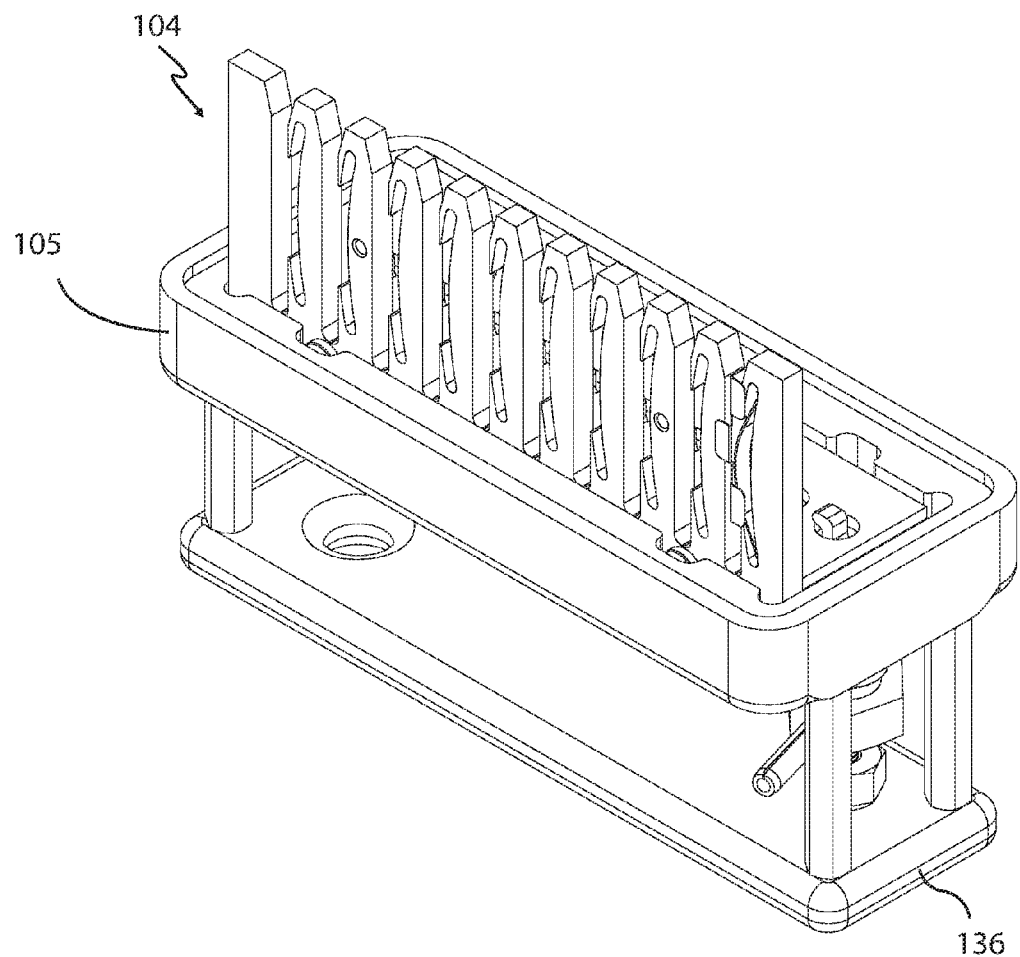
FIG. 1H shows another side view of the slide holder shown in FIG. 1A.
Figure 2:
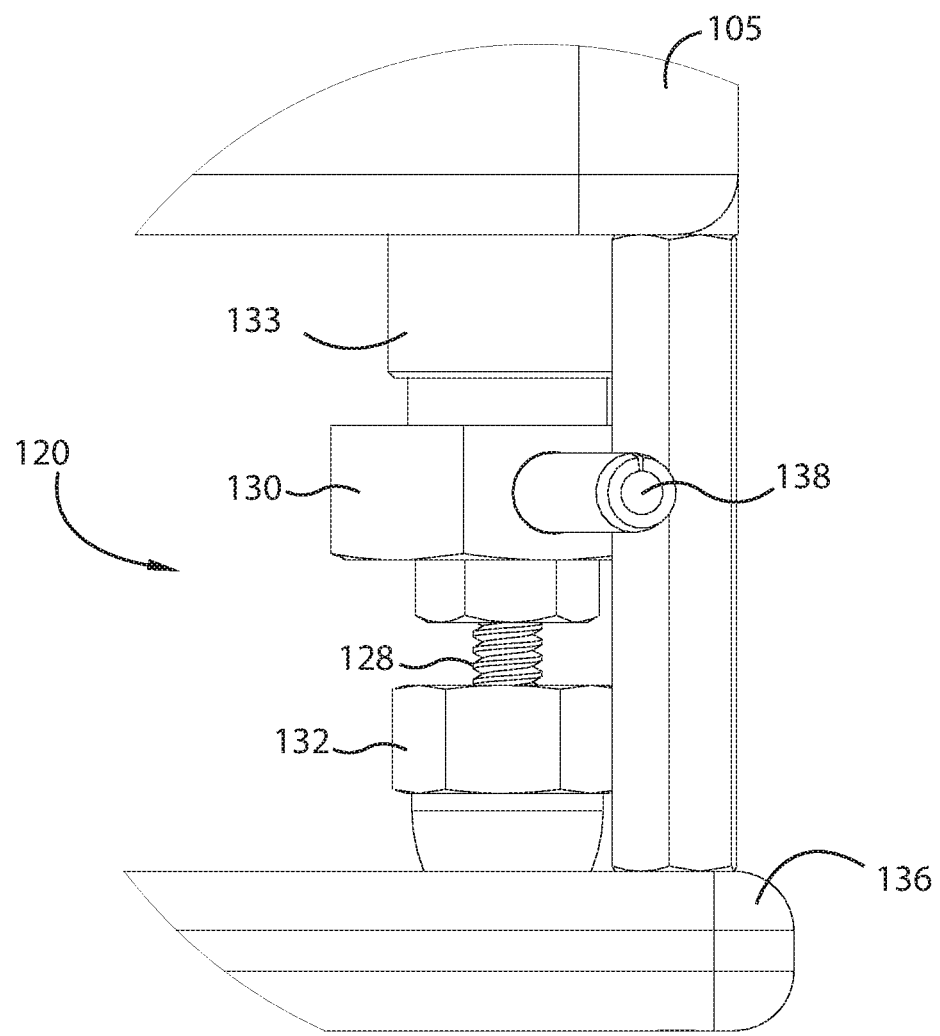
FIG. 2 shows a close-up view of section B shown in FIG. 1D.
Figure 3A:
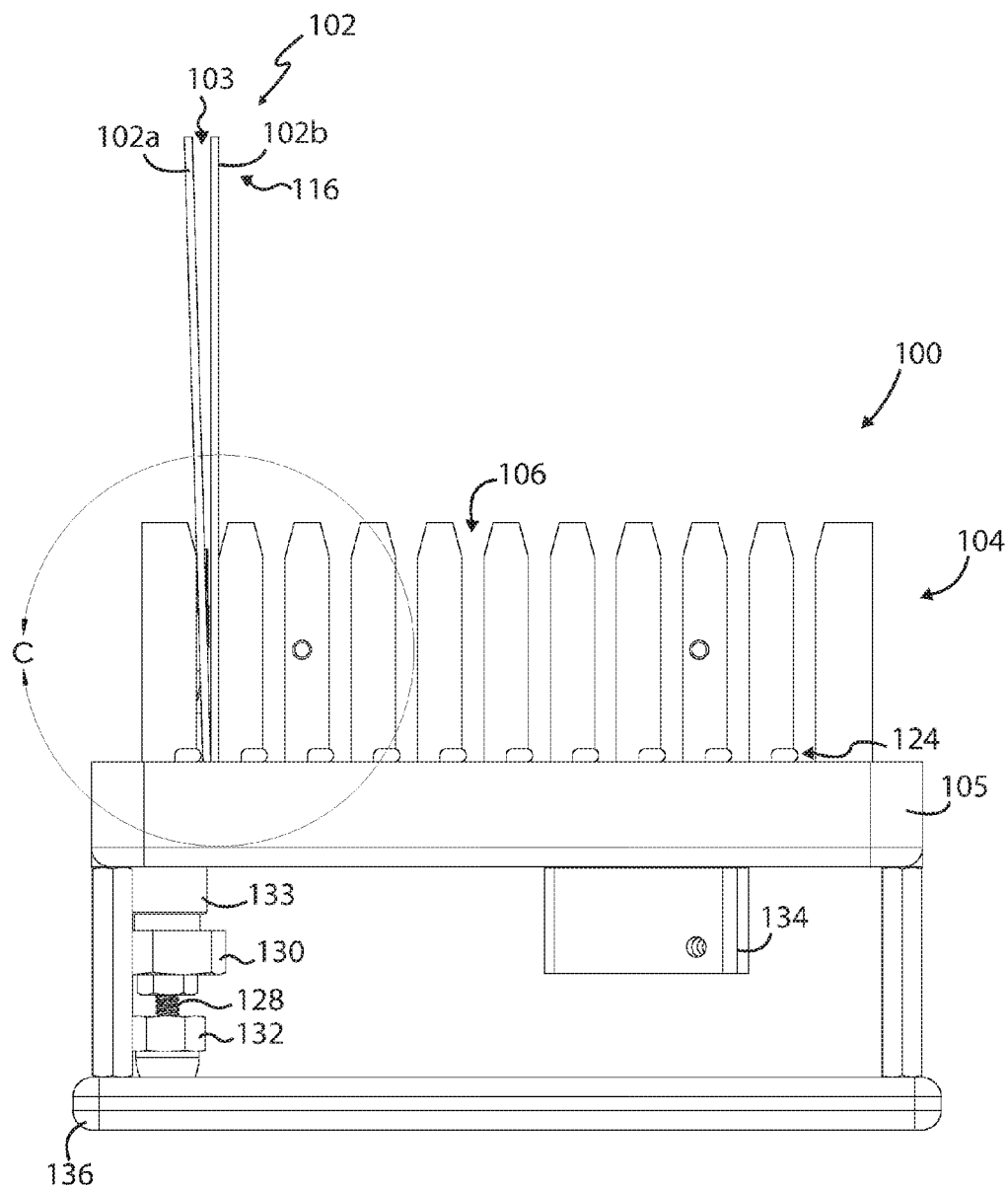
FIG. 3A shows another side view of an embodiment of the slide holder with one slide pair installed.
Figure 3B:
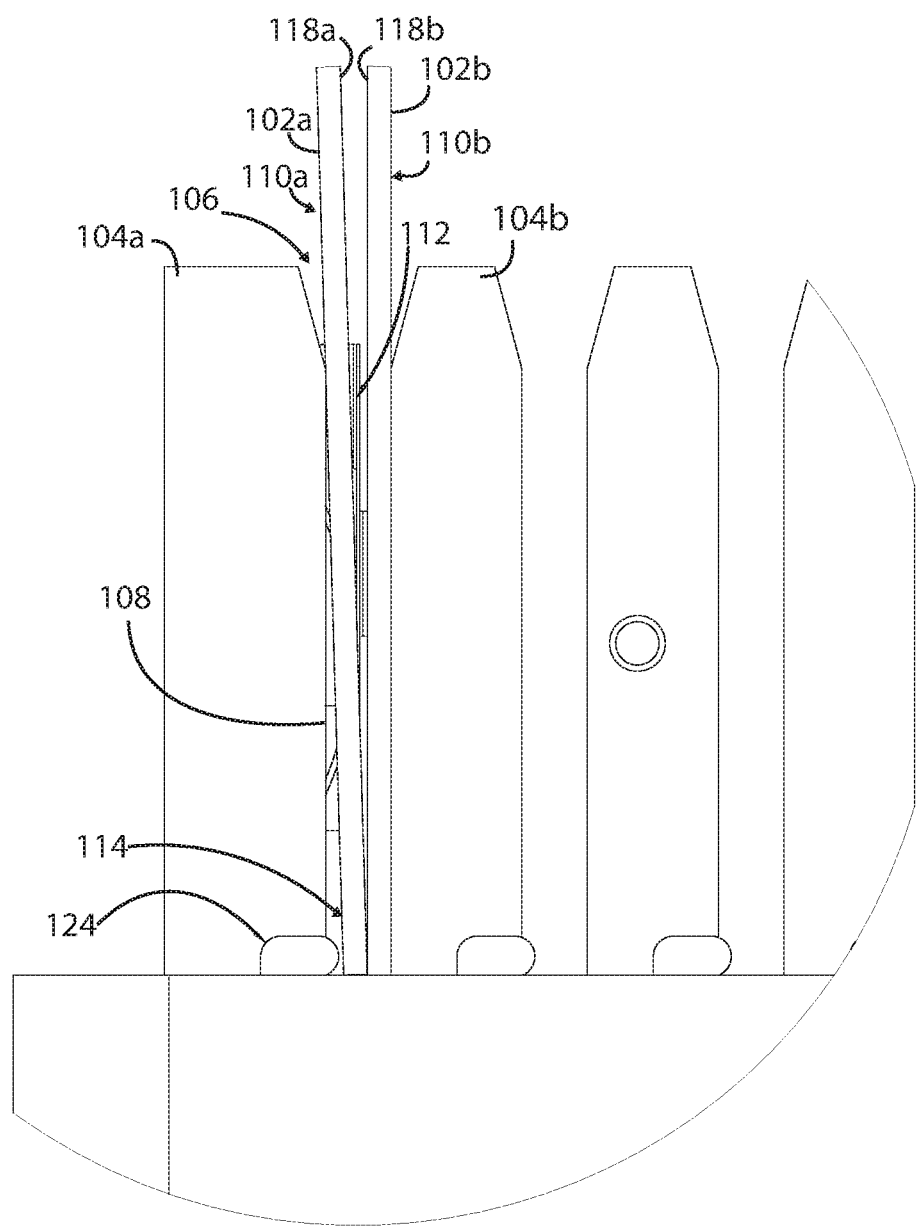
FIG. 3B shows a close-up view of section C shown in FIG. 3A.

In some embodiments, rather than a single shim spanning across the entire width of the slide pair 102a, 102b, a pair of half shims 119 may be used. The half shims are not necessarily half the width of the full shims. In some embodiments, the half shims may be less than half the width of the full shim. Regardless, the half shims comprise forward tabs 113a and rearward tabs 115a on the same side, but only on one side as shown in FIG. 1G. Two of the half shims 119 can be placed against opposite edges of the slide pair 102a, 102b to serve the same function as the full shim. In embodiments in which the half shim is less than half the width of the full shim a space would exist in between the edges of the half shim that do not have the tabs. If desired, a specimen could reside in that space between the shims.

In the preferred embodiment, the slide holder 100 is capable of forming a capillary gap 103 between slides within a slide pair 102a, 102b where the size of the capillary gap 103 so formed is adjustable by increasing or decreasing the distance separating the adjacent slides 102a, 102b. An adjustable capillary gap 103 is formed when the slides 102a, 102b are loaded by positioning the spacer 112 between adjacent slides 102a, 102b. The thickness of the spacer 112 sets the initial gap size. In the preferred embodiment, the gap size ranges from approximately 50 to approximately 250 microns, although any gap capable of supporting capillary action for particular liquids may be used.

The capillary gap 103 provides the means for introducing processing fluids on to the surface of the biological specimens adhered to the slides. Processing fluids and reagents the same thing and are used interchangeably to refer to buffers, solvents, reactants, chemicals, and the like used in various experiments, such as immunocytochemistry, immunohistochemistry, in situ hybridization, and the like.

The adjustable gap 103 can be repeatedly increased or decreased in size. This action creates a pulsatile movement of the processing reagent across the surface of the biological specimen. The pulsatile movement of the processing fluid across the surface of the biological specimen facilitates mixing of the processing fluid and greatly facilitates the required chemical reactions.

Any mechanical device that creates an adjustable gap 103 between two parallel microscope slides 102a, 102b could be used as the capillary gap adjuster 120. In the preferred embodiment, the capillary gap adjuster 120 may be attached to the cover 105. As best seen in FIG. 4, the capillary gap adjuster 120 may comprise a slide rack 122 having a plurality of protuberances 124, at least one protuberance 124a corresponding with each slide pair 102a, 102b. The slide rack 122 may be housed within the cover 105 with the protuberances 124 projecting out from the cover 105 in the same direction as the posts 104. The slide rack 122 and the posts 104 are arranged such that when the slide pairs 102a, 102b are inserted in between their two respective posts 104a, 104b, at least one protuberance 124 is adjacent to the same respective outer side 110a of each slide pair 102a, 102b at the first end 114 of the slide pair 102a, 102b.

The slide rack 122 is configured to slide in a longitudinal direction relative to the cover 105. The sliding action causes the protuberances 124 to pinch their respective first slide 102a toward their respective second slide 102b of each slide pair at the first end 114. The spacer 112 is positioned medially inwardly relative to the first end 114, thereby creating a space between the slides of the slide pair 102a, 102b at the first end 114. Therefore, the spacer 112 acts as a fulcrum upon which the first slide 102a can pivot or rock. When the first end 114 of a slide pair 102a, 102b is pinched together by a protuberance 124a, the second end 116 of the slide pair 102a, 102b separates, thereby enlarging the capillary gap 103.

In the preferred embodiment, the capillary gap adjuster 120 comprises a piston 126 that abuts against the slide rack 122. The piston 126 may comprise a threaded body 128. A nut 130 is mounted on the threaded body 128 of the piston 126 such that the rotational movement of the nut 130 about the threaded body 128 causes linear movement of the piston 126. A mount 132 may be provided to stabilize the piston 126 at the opposite end of the slide rack 122. For ease of actuation, an actuator 134 may be operatively connected to the nut 130, such that actuation of the actuator 134 causes rotation of the nut 130. For example, the actuator 134 may be operatively connected to the nut 130 through a series of gears (not shown). In another embodiment, the nut may comprise an arm 138. The actuator 134 may be connected to the arm 138 with a rod (not shown) such that actuation of the actuator 134, pulls and pushes the arm 138 to cause the nut 130 to rotate in a clockwise and counterclockwise direction about the threaded body 128.

Therefore, the nut 130 is operatively connected to the actuator 134 such that movement of the actuator 134 in a first direction rotates the nut 130 in a first rotational direction, and movement of the actuator 134 in a second direction rotates the nut 130 in a second rotational direction. The piston 126 is operatively connected to the nut 130 such that rotation of the nut 130 in the first rotational direction causes linear movement of the piston 126 in a first linear direction, and rotation of the nut 130 in the second rotational direction causes linear movement of the piston 126 in a second linear direction opposite the first linear direction. A guide 133 may be provided to facilitate linear movement of the piston 126.

The slide rack 122 is operatively connected to the piston 126 such that movement of the piston 126 in the first linear direction causes movement of the slide rack 122 in a third linear direction, and movement of the piston 126 in he second linear direction causes movement of the slide rack 122 in a fourth linear direction. The slide rack 122 is operatively connected to the slide pair 102a, 102b such that movement of the slide rack 122 in the third linear direction causes the first end 114 of the slide pair 102a, 102b to pinch towards each other, and movement of the slide rack 122 in the fourth linear direction allows the first end 114 of the slide pair 102a, 102b to move apart. When the first end 114 of the slide pair 102a, 102h is pinched together the capillary gap 103 grows at the second end 116 and when the first end 114 of the slide pair 102a, 102b moves apart, the capillary gap 103 shrinks at the second end 116. The shrinking and growing of the capillary gap 103 causes any processing fluid within the capillary gap 103 to move along the length of the slide pair 102a, 102b. When the actuator 134 is actuated repeatedly, it creates a pulsatile flow of the processing fluid thereby mixing the processing fluid along the biological sample. In some embodiments, the actuator may be a button that automatically and electrically moves the slide rack back and forth to create the pulsatile flow. In addition to the configurations described above, any number of configurations may be employed to use a spacer or shim to create a capillary gap and as a fulcrum to adjust the capillary gap while two ordinary microscope slides are in a holder for processing biological samples.

To facilitate handling of the slide holder 100, the slide holder 100 may comprise a handle 136. The handle 136 n may be attached to the cover 105 with the capillary gap adjuster 120 mounted therebetween. The handle 136 allows the slide holder 100 to be carried in the proper orientation to be dipped in various reagents as discussed in further detail below.

Other possible structural variations of the slide rack include: 1) slide racks with a larger capacity for accepting slide pairs, 2) slide pairs spatially positioned in a different arrangement, and 3) single slides with another parallel surface, not a microscope slide, for forming a capillary gap between the microscope slide and the parallel surface.

Reagent Holder

Figure 5A:
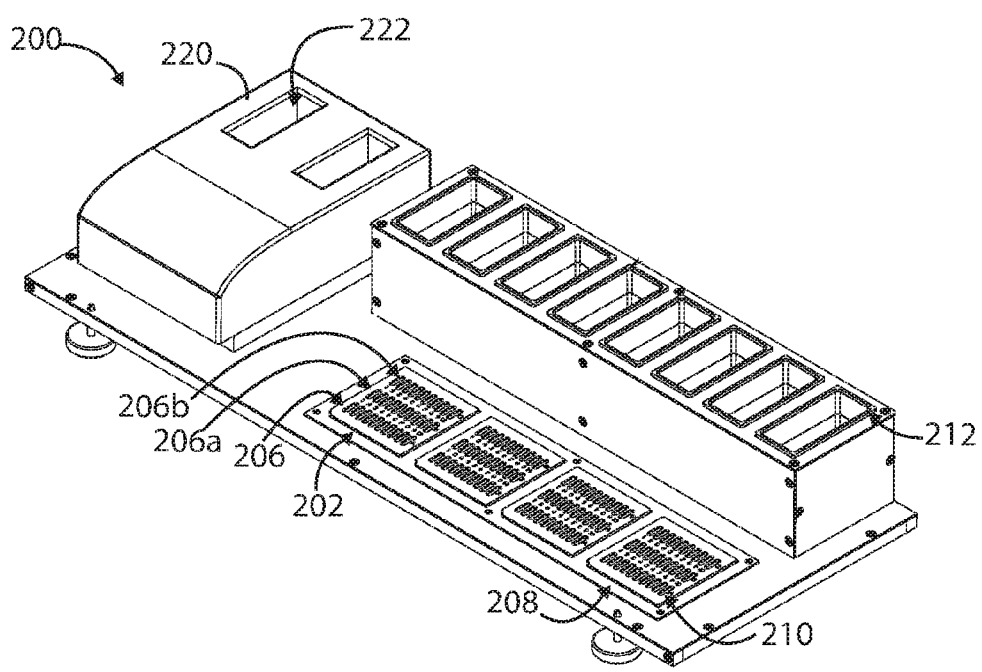
FIG. 5A shows a perspective view of another embodiment of the present invention without the slide holder.
Figure 5B:
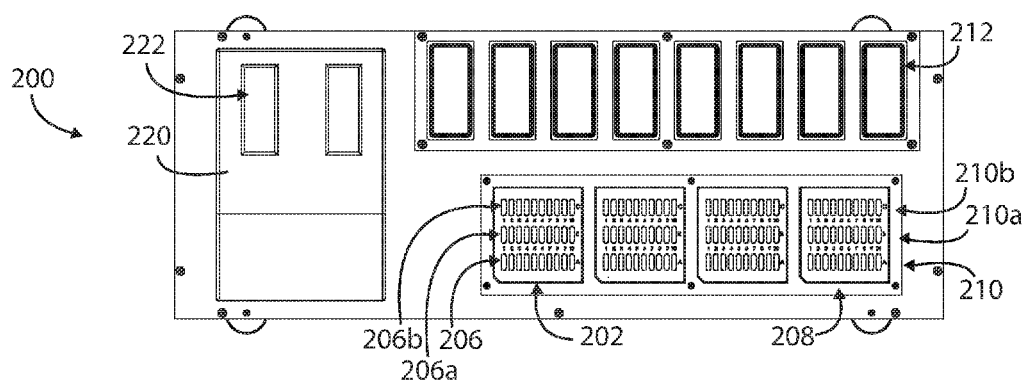
FIG. 5B shows a top view of the embodiment shown in FIG. 5A.

As shown in FIGS. 5A-5B, in some embodiments, he system can be provided as a kit 200 with other components to facilitate the processing of the biological specimens. For example, in addition to the slide holder 100, the kit 200 may further comprise a reagent holder. There may be two methods of applying reagents or processing fluids to the biological specimen. The first method involves treating each slide pair 102a, 102b within a slide holder 100 with its unique reagent or processing fluid. In this method, the reagent holder may be a reagent tray 202. In another method, all of the slide pairs 102a, 102b within a slide holder 100 are treated with the same reagent or processing fluid. In this method, the reagent holder may be a reagent bath 212.

The reagent tray 202 may comprise one or more troughs 206. The troughs 206 are configured to contain the processing fluids. The troughs 206 are arranged in a pattern identical to the slide arrangement in the slide holder 100 so that the second ends 116 of each slide pair 102a, 102b can be dipped in a separate trough 206 simultaneously, where each trough 206 contains a unique processing fluid intended for only one slide pair 102a, 102b. When the second ends 116 of each slide pair 102a, 102b are dipped into the reagent, the reagent is immediately drawn up the capillary gap 103 by means of capillary action, thus coming into contact with the mounted biological specimens. In this case one slide pair 102a, 102b may be treated with the processing fluid in its corresponding trough 206 whereas a neighboring slide pair may be treated with another type of processing fluid. The reagent tray 202 could contain a different number of troughs 206, the troughs 206 could be arranged differently, or the troughs 206 could be made to hold more or less of a processing fluid. In some embodiments, the reagent tray 202 may comprise several rows of troughs 206, 206a, 206b so that the slides 102 may be serially dipped in one set of troughs 206, then another set of troughs 206a, then another set of troughs 206b. Depending on the protocol, the reagents can be removed, and optionally washed, in between treatments.

Figure 6:
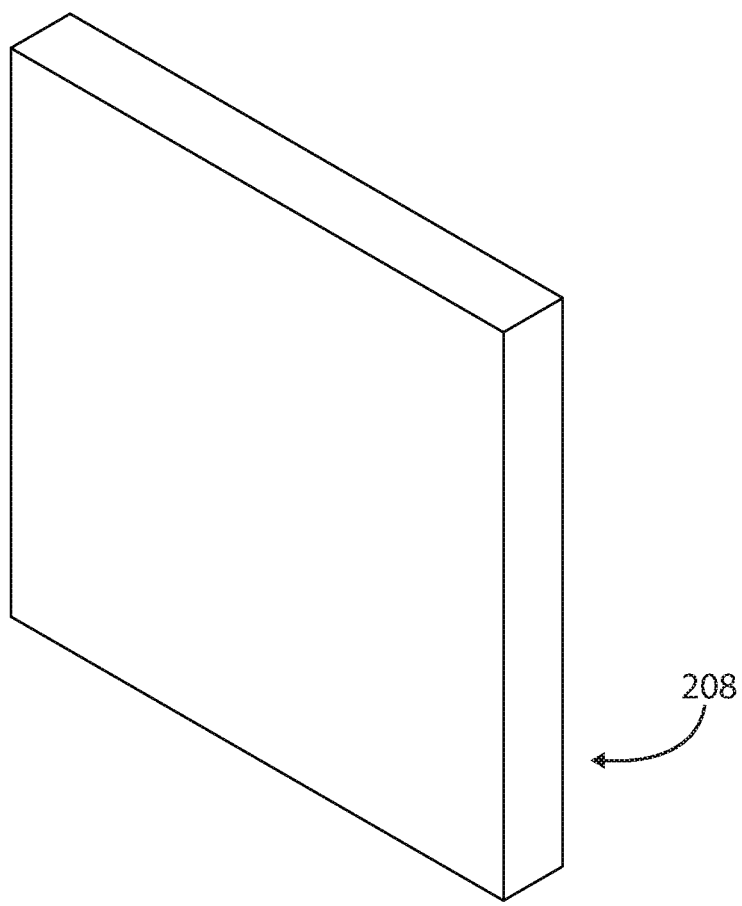
FIG. 6 shows an embodiment of the absorbent pad.

To accomplish this, the kit 200 may farther comprise an absorbent pad 208, as shown in FIG. 6, capable of contacting the ends 116 of the slide pairs 102a, 102b causing the withdrawal of the processing fluids from the slide pairs 102a, 102b. In the preferred embodiment, the absorbent pad 208 may be constructed of an absorbent material such as cellulose. Other types of absorbent materials of cellulose, derived from various plant sources or other synthetic materials could be used. Therefore, the capillary action can be reversed and the reagent removed from the capillary gap 103 by touching the second end 116 of the slide pair 102a, 102b to the absorbent pad 208. This effectively removes a first reagent from the slide pairs 102a, 102b in preparation for the application of the next reagent. To facilitate drainage, the capillary gap 103 may be increased before or while the slide pairs are touched to the absorbent pad 208, which result in more complete drainage than fixed gap slides.

Figures 7A, 7B:
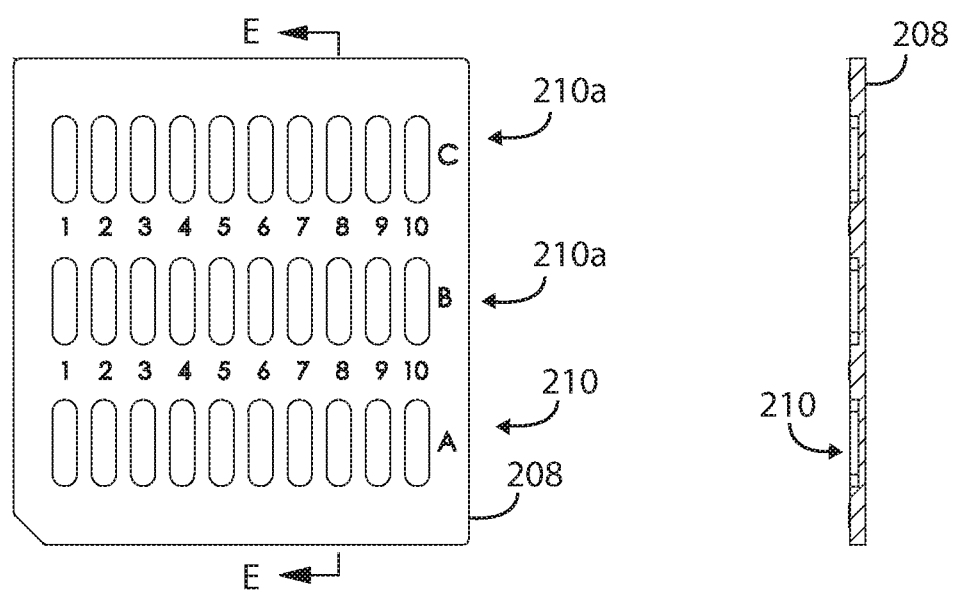
FIG. 7A shows a top view of an embodiment of the reagent holder.
FIG. 7B shows a cross-sectional view of the reagent holder shown in FIG. 7A taken through line E-E.

In the preferred embodiment, as shown in FIGS. 7A-7B, the absorbent pad 208 may comprise absorbent wells 210, 210a, 210b that align with the slide pairs 102a, 102b just like the troughs 206 of the reagent tray 202. This reduces the possibility of cross-contamination of reagents of adjacent slides 102 in the slide holder 100. The wells 210, 210a, 210b are simply recesses or indentations within the absorbent pad 208, and therefore the wells 210, 210a, 210b are also absorbent and capable of withdrawing the reagent from in between the capillary gap 103 of each slide pair 102a, 102b. Alternatively, the absorbent pad may 208 may not have its own indentations, but may have a cover that has openings that correspond to the indentation locations.

Aside from dipping each independent slide pair 102a, 102b in separate reagents, the kit may be provided with a reagent bath 212 in which all of the slides 102 within a slide holder 100 are dipped or submerged into the same reagent. A. plurality of reagent baths 212 may be provided where each bath contains a hulk processing fluid. Each reagent bath 212 may be capable of accepting a slide holder 100 containing multiple pairs of microscope slides 102, where all of the slide pairs 102a, 102b within the slide holder 100 are exposed to the same processing fluid.

Figure 8:
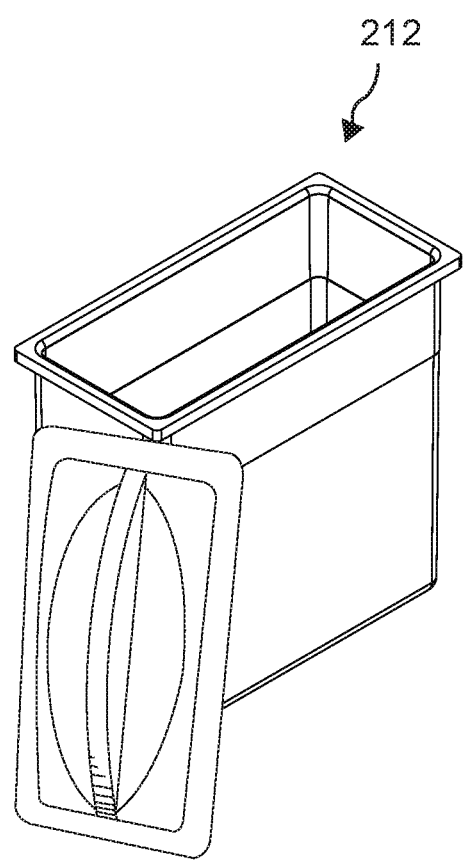
FIG. 8 shows a perspective view of another embodiment of a reagent holder.

Reagent baths 212 are used for delivering bulk reagents to all slides contained within a slide holder 100. For example, in certain steps of the staining process it is desirable to treat all slides 102 with the same reagent. In such instances a reagent bath 212 is used. With reference to FIG. 8, the reagent bath 212 is a container open at the top into which the slide holder 100 can be inserted. The reagent bath may hold about 5 milliliters to about 20 milliliters of a bulk processing fluid. When the ends 116 of the slide pairs 102a, 102b are submerged or dipped into the reagent of the reagent bath 212, the reagent is immediately drawn into the capillary gap 103 and comes into contact with the mounted biological specimen.

Any open container capable of receiving a slide holder 100 containing multiple slide pairs 102a, 102b can be used. In the preferred embodiment, each reagent bath 212 is deep enough to receive up to the cover 105 of the slide holder 100, and the opening of the reagent bath 212 is configured to substantially match the dimensions of the cover 105. In this configuration, all of the slides 102 mounted on the slide holder 100 can be submerged in the reagent bath 212 and the cover 105 of the slide holder 100 can close the opening of the reagent bath 212. The cover 105 can, therefore, minimize or prevent any evaporation or reduce contamination of the reagent when the slides 102 are left in the reagent bath 212 for a prolonged period of time.

Figure 9:
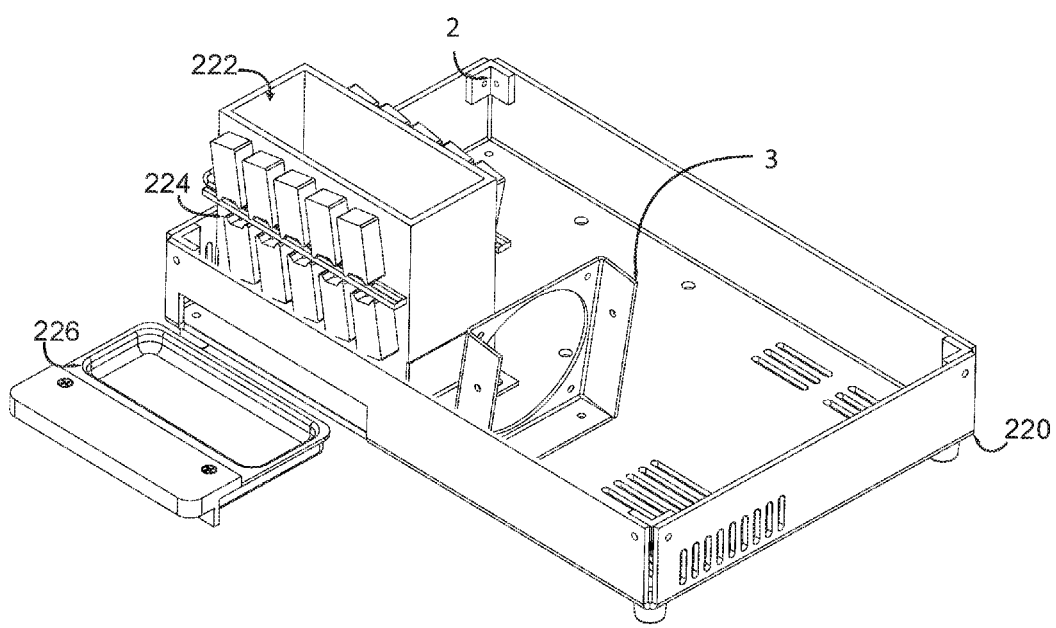
FIG. 9 shows an embodiment of the incubator with the top removed to show inside the incubator.

In certain processes it is necessary to incubate the reagent and biological specimens at specific temperatures in order to initiate the desired chemical reaction. Therefore, the kit 200 may further comprise an incubator 220 that can establish a standard temperature. With reference to FIG. 9, the incubator 220 comprises a heating element 224 and a compartment 222. In some embodiments, the compartment 222 may be configured to have the same dimensions as the reagent bath 212 for holding a slide holder 100. The heating element is operatively connected to the compartment 222 to be able to heat the reagent the compartment 222 to a desired temperature, for example, temperatures of greater than 100 degrees Celsius. In some embodiments, the compartment 222 may be configured to receive the reagent bath 212 with the heating element 224 capable of heating the reagent in the reagent bath 212. This facilitates quick and easy exchanges of reagent baths 212 within the incubator 220. In either embodiment, the opening of the compartment 222, like the opening of the reagent bath 212 is configured so that the cover 105 of the slide holder 100 can cap the opening so as to prevent evaporation and contamination. The incubator 220 may come in its own cap 226 to cover the compartment 222 when the slide holder 100 is not in use.

The incubator 220 provides a constant temperature environment for facilitating certain chemical reactions. Furthermore the incubator 220 can hold a processing fluid necessary for contacting the biological specimen and provides a closed system hat prohibits evaporation. Any combination of sealed chamber, heating element, and temperature controller could provide essentially the same function.

Operation of Preferred Embodiment

This invention describes a method for manipulating microscope slides containing mounted biological specimens for the purpose of processing, staining, and evaluating said biological specimens in order to extract relevant information from the cell or tissue sample, such as molecular information. The invention utilizes a capillary gap 103 formed between two adjacent microscope slides 102a, 102b that facilitate the addition and removal of various processing fluids by drawing the e fluids into the capillary gap 103 between the two slides 102a, 102b such that the processing fluid comes into contact with the biological samples.

One method of staining molecular structures in tissues is by a process known as immunohistochemistry (IHC). An important part of this procedure is a series of steps whereby processing fluids are contacted with the biological sample. This inventions describes a novel device that positions two ordinary microscope slides 102a, 102b, with a biological sample mounted onto at least one of the slides, into close proximity to each oilier but separated by a spacer 112 such that a s mall capillary gap 103 is formed between the two facing inner sides 118a, 118b. Processing fluids can be added to the slides by inserting one end 116 of the slide pairs 102a, 102b into a reagent and allowing the reagent to flow upward by capillary action until the capillary gap 103 is filled with processing fluid and the biological specimen is covered. After the appropriate reaction has taken place, the processing fluid is removed from the capillary gap 103 by touching the end 116 of the slide pair 102a, 102b to an absorbent pad 208, which will reverse the capillary flow and draw the processing fluid out of the capillary gap and into the absorbent pad 208. Having emptied the gap 103, the slide pair 102a, 102b is now ready to receive the next processing fluid. This sequence of steps, filling, incubating, and emptying the capillary gap, forms the basic reaction step that is repeated multiple times with different processing fluids until the final reaction has been achieved.

Another important aspect of the current invention is that the capillary gap 103 between the slides of a slide pair 102a, 102b can be adjusted to make the gap 103 smaller or larger, The smaller gap facilitates loading of reagent into the gap 103 by allowing the fluid to flow vertically up the capillary space. Likewise increasing the size of the capillary gap 103 facilitates removal of processing fluids by inducing the fluid to move down the capillary space. Furthermore, the processing fluid can be induced to move up and down the capillary space by repeatedly increasing and decreasing the capillary space. This creates a pulsatile movement of the fluid across the biological specimen, creates mixing, and greatly facilitates the chemical reaction. The pulsatile movement of processing fluid results in increased reaction of the processing fluid on the biological sample, which reduces incubation times, increases stain intensity, and diminishes stain variability across the specimens. It also increases the effectiveness of the reagent, which in some cases can allow more samples on each slide to be processed, which decreases overall reagent use. In addition, increasing the capillary gap while draining the slides onto an adsorbent pad causes the processing fluid to drain more completely than a fixed capillary gap slide, which requires less rinsing of the slides between reactive steps. With typical capillary gap slides, it requires 6-10 rinses between steps, With the adjustable gap slides, it take as few as 3 rinses, reducing the processing time and effort.

By way of example only, in use, the user takes a spacer 112 and two standard microscope slides 102a, 102b and sandwiches the spacer 112 in between the two slides 102a, 102b, thereby forming a slide pair with what has become the inner surfaces 118a, 118b of the slide pair 102a, 102b facing each other. Prior to this step, at least one biological specimen would have been adhered to at least one of the inner surfaces 118a, 118b. The end of the slide pair 102a, 102b closer to the spacer 112 is referred to as the first end 114, and the end of the slide pair 102a, 102b adjacent to the biological specimen is referred to as the second end 116 of the slide pair 102a, 102b. The user can then take the slide pair 102a, 102b and insert the e first end 114 of the slide pair 102a, 102b in a groove 106 defined by two posts 104a, 104b of a slide holder 100. One or both posts 104a, 104b may have one or more retaining springs 108 associated therewith to create a biasing force against the outer surfaces 110a, 110b of the slide pair 102a, 102b at the position of the spacer 112. This keeps the slide pair 102a, 102b together; however, due to the spacer 112, a capillary gap 103 exists between the inner surfaces 118a, 118b of the slide pair 102a, 102b. This loading process may be repeated until all of the grooves 106 defined by a pair of posts 104 are filled with slide pairs with spacers 112 defining a capillary gap 103, and with the biological specimen contained within the capillary gap 103.

The user can then grab the handle 136 of the slide holder 100 so that the second ends 116 of each of the slide pairs 102a, 102b are hanging below the slide holder 100. Depending on the protocol, the user can dip the second ends 116 of each of the slide pairs 102a, 102b into one of the reagent holders. For example, the user may simultaneously dip each of the second ends 116 of the slide pairs 102a, 102b into a reagent tray 202. Each trough 206 of the reagent tray 202 may have a different reagent or the same reagent. By dipping only the second ends 116 of the slide pairs 102a, 102b, the reagent is taken up into the capillary gap 103 via capillary action.

The user can then use the actuator 134 of the slide holder 100 to repeatedly cause the slide rack 122 to prove against and away from the outer surface 110a of one of the slides 102a at the first end 114 in each of the slide pairs 102a, 102b. This pulsatile action causes one of the slides 102a in the slide pair 102a, 102b to pivot about the spacer 112 which causes the slides within the slide pair 102a, 102b to move towards and away from each other which enlarges and shrinks the capillary gap 103. This causes the reagent within the capillary gap 103 to move throughout the capillary gap 103 to mix the reagent thoroughly with the biological specimen. The mixing of the processing fluids can improve the staining process by shone incubation times, increasing stain intensity, and reducing stain variability.

Alternatively and/or subsequently, the slides may be inserted into a reagent bath 212. In this scenario, each of the biological specimens on the slides 102 would be exposed to the same reagent at the same time. When using a reagent bath 212, the entire slide 102 may be submerged in the reagent, or the reagent bath 212 may only contain a shallow pool of the reagent at the bottom of the reagent bath 212, and the reagent is taken up through capillary action just like the reagent tray 202. Furthermore, with the reagent bath 212, the cover 105 of the slide holder 100 may be used to cap the opening of the reagent bath 212 so as to leave the slides 102 in the reagent bath 212 for a prolonged period of time. Due to the cover 105, evaporation and contamination is controlled. Like the reagent tray 202, the reagent may be mixed within the capillary gap 103 with the capillary gap adjuster 120. In some embodiments, the reagent bath 212 may be in an incubator 220. The incubator 220 can increase the temperature of the reagent in the reagent bath 212 to a desired temperature. By way of example only, the incubator 220 may be set to any temperature between ambient temperature and approximately 120 degrees C.

Whether the reagent tray 202 or the reagent bath 212 was used, when the user is ready to place the biological specimen into the next reagent, the current reagent will have to be removed, To do so, the user lifts the slide holder 100 from the reagent, and places the second end 116 of each of the slide pairs 102a, 102b on to an absorbent pad 208. The absorbent pad 208 then removes the reagent from in between the capillary gaps 103 via a reverse capillary flow. The liquid flows out of the capillary space and into the absorbent pad where it can be disposed of. This reverse capillary flow can be further facilitated by increasing the capillary gap space using the capillary gap adjuster 120. The slide pairs 102a, 102b are now ready for the next reagent, whether it be for a wash, rinse, or a chemical reaction.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A system for processing biological specimens, comprising:
   a. a plurality of slides;
   b. a plurality of spacers, one spacer placed in between two slides to create a slide pair, the slide pair having a pair of inner surfaces adjacent to each other and separated by a capillary gap, and a pair of outer surfaces on opposing sides;
   c. a slide holder, comprising:
      i. a plurality of posts serially arranged on a cover, wherein a groove is defined in between adjacent posts for receiving one slide pair,
      ii. a plurality of retaining springs, wherein for each slide pair, a first retaining spring biases against a first post and a first outer surface of the slide pair,
      iii. a capillary gap adjuster, comprising a actuator, a nut operatively connected to the actuator such that movement of the actuator in a first direction rotates the nut in a first rotational direction, and movement of the actuator in a second direction rotates the nut in a second rotational direction, a piston operatively connected to the nut, wherein rotation of the nut in the first rotational direction causes linear movement of the piston in a first linear direction, and rotation of the nut in the second rotational direction causes linear movement of the piston in a second linear direction opposite the first linear direction, and a slide rack operatively connected to the piston, wherein movement of the piston in the first linear direction causes movement of the slide rack in a third linear direction, and movement of the piston in the second linear direction causes movement of the slide rack in a fourth linear direction, wherein the slide rack is operatively connected to the slide pair such that movement of the slide rack in the third linear direction causes a first end of the slide pair to pinch together, and movement of the slide rack in the fourth linear direction allows the first end of the slide pair to move apart, wherein when the first end of the slide pair is pinched together the capillary gap grows and wherein when the first end of the slide pair moves apart, the capillary gap shrinks;
   d. a reagent tray comprising a plurality of troughs, wherein the troughs are spaced apart to correspond with each of the slide pairs on the slide holder so that each slide pair can be dipped into one trough simultaneously;
   e. a reagent bath configured to receive all slide pairs on the slide holder, the reagent bath defining an opening substantially similar in size to the cover such that the cover can cap the opening when the slide pairs are inside the reagent bath;
   f. an incubator for heating the reagent bath; and
   g. an absorbent pad for removing a reagent from the capillary gap when the slide pair contacts the absorbent pad.

2. A system for exposing a biological specimen to a reagent, comprising:
   a. a slide holder comprising:
      i. a cover;
      ii. a plurality of posts serially arranged along the cover, wherein a groove is defined in between adjacent posts for receiving one slide pair; and
      iii. a plurality of retaining springs for securing slide pairs against their respective posts;
   b. a plurality of spacers for separating slides within the slide pairs to create a capillary gap between the slides of each slide pair, wherein for each spacer, the spacer is positioned in between a first end of the respective slide pair and the second end of the respective slide pair to function as a fulcrum to allow the capillary gap at the second end of the slide pair to grow and shrink.

3. The system of claim 2, wherein the slide holder further comprises a capillary gap adjuster for adjusting the capillary.

4. The system of claim 3, wherein the capillary gap adjuster comprises:
   a. an actuator;
   b. a nut operatively connected to the actuator such that movement of the actuator in a first direction rotates the nut in a first rotational direction, and movement of the actuator in a second direction rotates the nut in a second rotational direction;
   c. a piston operatively connected to the nut, wherein rotation of the nut in the first rotational direction causes linear movement of the piston in a first linear direction, and rotation of the nut in the second rotational direction causes linear movement of the piston in a second linear direction opposite the first linear direction; and
   d. a slide rack operatively connected to the piston, wherein movement of the piston in the first linear direction causes movement of the slide rack in a third linear direction, and movement of the piston in the second linear direction causes movement of the slide rack in a fourth linear direction, wherein the slide rack is operatively connected to each slide pair such that movement of the slide rack in the third linear direction causes the first end of each slide pair to pinch together, and movement of the slide rack in the fourth linear direction allows the first end of the slide pair to move apart, wherein when the first end of the slide pair is pinched together the capillary gap at the second end grows and wherein when the first end of the slide pair moves apart, the capillary gap at the second end shrinks.

5. The system of claim 4, further comprising a reagent tray comprising a plurality of troughs, wherein the troughs are arranged to correspond to the second ends of certain slide pairs on the slide holder.

6. The system of claim 5, wherein the plurality of troughs are arranged in sets and sized to fit a single slide pair, arranged so that each trough will correspond to a single slide pair.

7. The system of claim 4, further comprising a reagent bath, wherein the reagent bath comprises a container sized to accommodate the second ends of all the slide pairs.

8. The system of claim 7, wherein the reagent bath defines an opening dimensioned similar to the cover to permit the cover to cap the opening.

9. The system of claim 4, further comprising an incubator comprising compartments operatively connected to a heating element to heat the compartment, wherein the compartment is sized to accommodate the second ends of a plurality of slide pairs in the slide holder.

10. The system of claim 9, wherein the compartment is dimensioned to receive a reagent bath that is sized to accommodate the second ends of a plurality of slide pairs in the slide holder.

11. The system of claim 4, further comprising an absorbent pad.

12. The system of claim 11, wherein the absorbent pad comprises a plurality of wells arranged in sets, wherein each set comprises wells spaced apart to correspond with each slide pair.

13. The system of claim 2, further comprising a reagent tray comprising a plurality of troughs, wherein the troughs are arranged to correspond to the second ends of certain slide pairs on the slide holder.

14. The system of claim 13, wherein the plurality of troughs are arranged in sets and sized to fit a single slide pair, arranged so that each trough will correspond to a single slide pair.

15. The system of claim 2, further comprising a reagent bath, wherein the reagent bath comprises a container sized to accommodate the second ends of all the slide pairs.

16. The system of claim 15, wherein the reagent bath defines an opening dimensioned similar to the cover to permit the cover to cap the opening.

17. The system of claim 2, further comprising an incubator comprising compartments operatively connected to a heating element to heat the compartment, wherein the compartment is sized to accommodate the second ends of a plurality of slide pairs in the slide holder.

18. The system of claim 17, wherein the compartment is dimensioned to receive a reagent bath that is sized to accommodate the second ends of a plurality of slide pairs in the slide holder.

19. The system of claim 2, further comprising an absorbent pad.

20. The system of claim 19, wherein the absorbent pad comprises a plurality of wells arranged in sets, wherein each set comprises wells spaced apart to correspond with each slide pair.

* * * * *